United States Patent [19]

Nishiyama et al.

[11] 4,331,670
[45] May 25, 1982

[54] PYRIDYLANILINES

[75] Inventors: Ryuzo Nishiyama, Takatsuki; Kanichi Fujikawa, Moriyama; Takahiro Haga, Kusatsu; Tadaaki Toki, Moriyama; Kuniaki Nagatani; Osamu Imai, both of Kusatsu, all of Japan

[73] Assignee: Ishihara Sangyo Kaisha, Ltd., Osaka, Japan

[21] Appl. No.: 212,432

[22] Filed: Dec. 3, 1980

[30] Foreign Application Priority Data

Dec. 25, 1979 [JP] Japan .................. 54-168574

[51] Int. Cl.³ .................. C07D 213/61; C07D 213/26; A61K 31/44
[52] U.S. Cl. .................. 424/263; 546/297; 546/304; 546/309
[58] Field of Search .................. 546/297, 304, 309; 424/263

[56] References Cited

U.S. PATENT DOCUMENTS 3,926,611 12/1975 Tomlin et al. .................. 71/94
3,965,109 6/1976 Tomlin et al. .................. 546/304
4,140,778 2/1979 Dreikorn .................. 424/263

*Primary Examiner*—Alan L. Rotman
*Attorney, Agent, or Firm*—Oblon, Fisher, Spivak, McClelland & Maier

[57] ABSTRACT

A novel compound for combatting insect, mite, fungus or bacterium is a pyridylaniline represented by the following formula (I)

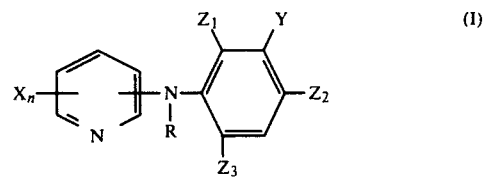

wherein X is a trifluoromethyl group, a halogen atom, a lower alkyl group or a lower alkoxy group; n is an integer of 0 to 4; R is a hydrogen atom or an acetyl group; Y is a hydrogen atom, a halogen atom a lower alkoxy group, a lower alkylthio group, a hydroxy group, an azido group or a phenoxy group of which the phenyl ring may be substituted by a hydroxy group; $Z_1$, $Z_2$ and $Z_3$ are a trifluoromethyl group or a nitro group, provided that at least one of X is a trifluoromethyl group or a lower alkyl group when n is an integer of 3 or 4.

19 Claims, No Drawings

PYRIDYLANILINES

BACKGROUND OF THE INVENTION

1. Field of the Invention

The present invention relates to a novel pyridylaniline for combatting insect, mite, fungus or bacterium.

2. Description of the Prior Art

It has been known that certain pyridylanilines have activities for combatting noxious livings such as insects, mites, fungi, bacteria and rodents in the prior arts, for example, the compounds having rodenticidal activity are disclosed in U.S. Pat. No. 4,140,778 and the compounds having pesticidal activity are disclosed in U.S. Pat. No. 3,965,109 and U.S. Pat. No. 3,926,611.

It has not been known that pyridylanilines having the specific substituents on pyridyl ring according to the present invention have activities for combatting noxious insect, mite, fungus, and bacterium.

SUMMARY OF THE INVENTION

It is an object of the present invention to provide novel pyridylanilines which are effective for combatting noxious insect, mite, fungus and bacterium.

It is another object of the present invention to provide novel compositions which have insecticidal, acaricidal, fungicidal and bactericidal activities.

It is the other object of the present invention to provide a process for producing the novel pyridylaniline.

The foregoing and other objects of the present invention have been attained by providing a pyridylaniline represented by the following formula (I)

$$X_n - \text{pyridyl} - N(R) - \text{phenyl}(Z_1, Y, Z_2, Z_3) \quad (I)$$

wherein X is a trifluoromethyl group, a halogen atom, a lower alkyl group or a lower alkoxy group; n is an integer of 0 to 4; R is a hydrogen atom or an acetyl group; Y is a hydrogen atom, a halogen atom a lower alkoxy group, a lower alkylthio group, a hydroxy group, an azido group or a phenoxy group of which the phenyl ring may be substituted by a hydroxy group; $Z_1$, $Z_2$ and $Z_3$ are a trifluoromethyl group or a nitro group, provided that at least one of X is a trifluoromethyl group or a lower alkyl group when n is an integer of 3 or 4.

DETAILED DESCRIPTION OF THE PREFERRED EMBODIMENTS

The pyridylanilines of the present invention can be the compounds having the formula (I) wherein the halogen atom can be F, Cl, Br or I and the lower alkyl group for the lower alkyl group, the lower alkoxy group or the lower alkylthio group can be $C_1-C_4$ alkyl groups such as methyl, ethyl, n-propyl, iso-propyl, n-butyl, iso-butyl, sec-butyl and tert-butyl groups.

The optional compounds included in the pyridylanilines having the formula (I) are the compounds having the formula (III), (V) or (X).

Formula (III); $X_n$—pyridyl—NH—phenyl($NO_2$, $Y_1$, $CF_3$, $NO_2$) (III)

Formula (V); $CF_3$—$X_m$—pyridyl—NH—phenyl($NO_2$, $Y_2$, $CF_3$, $NO_2$) (V)

Formula (X); $X_n$—pyridyl—NH—phenyl($NO_2$, $Y_3$, $CF_3$, $NO_2$) (X)

wherein X and n are defined above, and $Y_1$ represents hydrogen atom or a halogen atom; $Y_2$ represents hydrogen atom, a lower alkoxy group, a halogen atom, azido group, or phenoxy group which can be substituted by a hydroxyl group; $Y_3$ represents a lower alkoxy group, a lower alkylthio group, hydroxyl group, azido group or phenoxy group which can be substituted by a hydroxyl group; and m is an integer of 0 to 3. The most important pyridylanilines are the compounds having the formula (VII)

$$CF_3-\text{pyridyl}(X_4, X_5)-NH-\text{phenyl}(NO_2, Y_2, CF_3, NO_2) \quad (VII)$$

wherein $X_4$ is a halogen atom; $X_5$ is a hydrogen atom or a halogen atom; $Y_2$ is defined above.

The pyridylanilines of the present invention can be produced by the following processes.

REACTION (I)

Pyridylanilines having the formula (I) wherein R is hydrogen atom and Y is hydrogen or halogen atom The compounds are produced by the following reaction in the presence of a base.

$$X_n-\text{pyridyl}-U \;(A) \;+\; W-\text{phenyl}(Z_1, Y_1, Z_2, Z_3) \;(B) \xrightarrow{\text{base}}$$

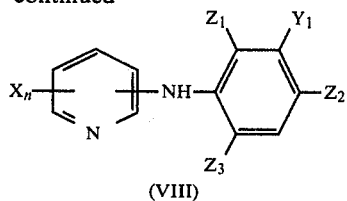

wherein X, $Y_1$, $Z_1$, $Z_2$, $Z_3$ and n in the formulas (A), (B) and (VIII) are defined above and U and W in the formulas (A) and (B) are respectively a halogen atom or amino group and W is amino group in the case of U of a halogen atom; and W is a halogen atom in the case of U of amino group.

The starting compounds (A) are mostly known and disclosed in U.S. Pat. No. 3,681,369, and E.P.O. Publication No. 0000483 etc.

The starting compounds (B) are mostly known and disclosed in U.S. Pat. No. 4,117,167 and E.P.O. Publication No. 0000156, and No. 0004642.

In the industrial process, it is preferable to react the compound (A) wherein U is amino group with the compound (B) wherein W is a halogen atom.

The base used in the reaction can be alkali metal hydroxides, carbonates, hydrides, or alkaline earth metal hydroxides and carbonates, preferably potassium hydroxide, sodium hydroxide, sodium hydride and sodium bicarbonate.

The reaction is preferably carried out in the presence of a solvent. Suitable solvents include aprotonic polar solvents such as dimethylformamide, dimethylsulfoxide, tetrahydrofuran, sulfolane and dioxane. It is preferable to use dimethylformamide or tetrahydrofuran. The reaction temperature is usually in a range of $-100°$ C. to $+200°$ C. preferably $0°$ to $200°$ C. and the reaction time is in a range of 0.5 to 24 hours especially 1 to 10 hours.

REACTION (II)

Pyridylanilines having the formula (I) wherein R is hydrogen atom and Y is hydroxyl group, a lower alkoxy group, a lower alkylthio group, azido group or phenoxy group which can be substituted by hydroxyl group The compounds are produced by the following reaction in the presence of a base

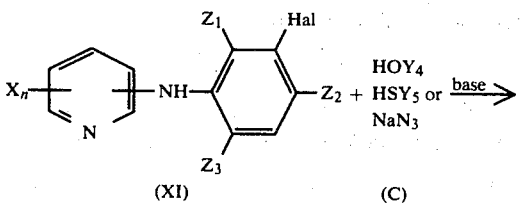

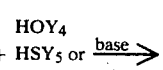

wherein X, $Y_3$ $Z_1$, $Z_2$, $Z_3$ and n in the formulas (X) and (XI) are defined above and Hal represents a halogen atom. In the formula (C), $Y_4$ represents hydrogen atom, a lower alkyl group or phenyl group which can be substituted by hydroxyl group; and $Y_5$ represents a lower alkyl group. The base used in the reaction is the same as the bases used in the former reaction (I).

The reaction is preferably performed in a solvent. The solvent can be the solvents used in the reaction (I) and alcohols such as methanol and ethanol, and halohydrocarbons such as carbon tetrachloride, chloroform and m-dichlorobenzene. The reaction temperature is usually in a range of $-30°$ C. to $+170°$ C. preferably $0°$ C. to $170°$ C. The reaction time is in a range of 0.5 to 20 hours.

In the reaction (II) using the starting compound having $Y_4$ of a hydroxy phenyl group, it is preferable to react them in nitrogen atmosphere. When the boiling point of the solvent is low, it is preferable to react them in a closed reactor.

REACTION (III)

Pyridylanilines having the formula (I) wherein R is acetyl group

The compounds are produced by the following reaction.

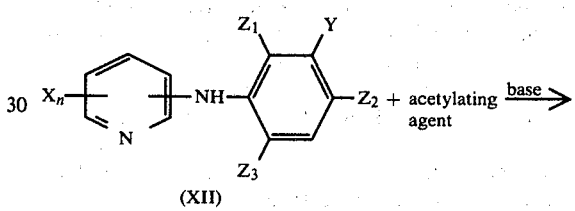

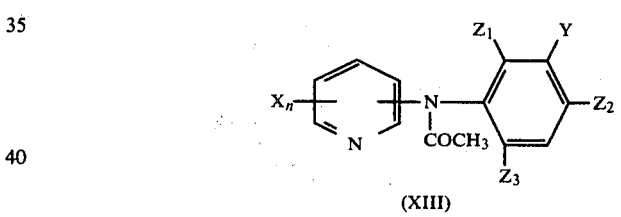

wherein X, Y, $Z_1$, $Z_2$, $Z_3$ and n in the formulas (XII) and (XIII) are defined above.

The acetylating agents can be anhydride, halides and esters of acetic acid, such as acetic anhydride, acetyl chloride, and ethyl acetate.

The base can be the bases used in reaction (I) and organic bases such as pyridine and triethylamine preferably organic bases. The reaction temperature is in a range of $0°$ to $100°$ C. The reaction time is in a range of 1 to 10 hours.

Certain examples of syntheses will be illustrated.

PREPARATION 1

Preparation of N-(3,5-dichloro-2-pyridyl)-2,6-dinitro-4-trifluoromethylaniline

In 20 ml. of dimethylformamide, 1.65 g. of 2-amino-3,5-dichloropyridine was dissolved and 1.0 g. of powdery potassium hydroxide was gradually added with stirring. After the addition, 2.7 g. of 2,6-dinitro-4-trifluoromethylchlorobenzene was added at $30°$ C. during 5 minutes and the reaction was continued for about 3 hours. The reaction mixture was acidified with conc. HCl and the product was extracted with methylenechloride. The extracted layer was washed with water and dehydrated. The solvent was distilled off and the product was separated by a silica gel column with an eluent of toluene and the solvent was distilled off to obtain 2.8 g. of the object compound having the melting point of 85° to 87° C.

PREPARATION 2

Preparation of N-(3,5-dichloro-6-methyl-2-pyridyl)2,6-dinitro-3-chloro-4-trifluoromethylaniline In 30 ml. of dimethylformamide, 1.8 g. of 2-amino-3,5-dichloro-6-methylpyridine was dissolved in 0.67 g. of powdery potassium hydroxide was gradually added with stirring. After the addition, a solution of 3.07 g. of 2,4-dichloro-3,5-dinitrobenzotrifluoride in 10 ml. of dimethylformamide was added dropwise at room temperature and the reaction was continued for about 3 hours. The reaction mixture was acidified with conc. HCl and was poured into water. The precipitate was filtered and recrystallized from methanol to obtain 2.96 g. of the object compound having a melting point of 128° to 130° C.

PREPARATION 3

Preparation of N-(3,5-dichloro-2-pyridyl)-2,6-dinitro-3-chloro-4-trifluoromethylaniline In 20 ml. of dimethylformamide, 1.63 g. of 2-amino-3,5-dichloropyridine was dissolved and 0.73 g. of powdery potassium hydroxide was added with stirring. After the addition, 3.06 g. of 2,4-dichloro-3,5-dinitrobenzotrifluoride was added during 10 minutes. The reaction was continued for about 2 hours. After the reaction, the reaction mixture was poured into water and acidified with conc. HCl and the product was extracted with methylene chloride. The extracted layer was washed with water and dehydrated and the solvent was distilled off and the product was separated by a silica gel column with an eluent of toluene and then the solvent was distilled off to obtain 1.38 g. of the object compound having the melting point of 64° to 65° C.

PREPARATION 4

Preparation of N-(3-chloro-5-triuoromethyl-2-pyridyl)-2,6-dinitro-3-chloro-4-trifluoromethylaniline

METHOD A

In accordance with the process of Preparation 3 except using 1.97 g. of 2-amino-3-chloro-5-trifluoromethylpyridine instead of 1.63 g. of 2-amino-3,5-dichloropyridine and adding 0.62 g. of powdery potassium hydroxide instead of 0.73 g. of the same, the process was carried out to obtain 1.15 g. of the object compound having the melting point of 100° to 102° C.

METHOD B

In 60 ml. of tetrahydrofuran, 3.22 g. of 2-amino-3-chloro-5-trifluoromethylpyridine was dissolved and 2.0 g. of powdery potassium hydroxide was gradually added with stirring and the mixture was cooled at 0° C., and a solution of 5.0 g. of 2,4-dichloro-3,5-dinitrobenzotrifluoride in 40 ml. of tetrahydrofuran was added dropwise at the same temperature and the mixture was heated to react them at room temperature for 3 hours. The reaction mixture was poured into water and 150 ml. of ethyl acetate was added and the mixture was acidified with conc. HCl and the product was extracted. The extraction solution was washed twice with water and dehydrated over anhydrous sodium sulfate and concentrated. The product was separated by a silica gel column with an eluent of a mixture of n-hexane and ethyl acetate (10:1) and the solvent was distilled off to obtain 6.5 g. of the object compound having the melting point of 100° to 102° C.

2-Amino-3-chloro-5-trifluoromethylpyridine used in Preparation 4 can be produced by the following process.

In a 50 ml. autoclave, 6.5 g. of 2,3-dichloro-5-trifluoromethylpyridine and 20 ml. of 28% ammonia water were charged and stirred at 100° C. for 24 hours and heated at 125° C. for 5 hours to react them (pressure of about 2 atm.). After cooling the reaction mixture, the resulting crystal was washed with water and dehydrated to obtain 1.5 g. of 2-amino-3-chloro-5-trifluoromethylpyridine having the melting point of 90° to 92° C.

PREPARATION 5

Preparation of N-(3,5-dichloro-4-pyridyl)-2,6-dinitro-4-trifluoromethylaniline

In accordance with the process of Preparation No. 2 except using 1.63 g. of 3,5-dichloro-4-aminopyridine instead of 1.8 g. of 2-amino-3,5-dichloro-6-methylpyridine; and using 50 ml. of dimethylformamide instead of 30 ml. of the same and using 2.7 g. of 2,6-dinitro-4-trifluoromethylchlorobenzene instead of 3.07 g. of the same, the process was carried out to obtain 2.8 g. of the object compound having the melting point of 138° to 140° C.

PREPARATION 6

Preparation of N-(3,5-dichloro-2-pyridyl)-2,4-dinitro-6-trifluoromethylaniline

In 20 ml. of dimethylformamide, 1.65 g. of 2-amino-3,5-dichloropyridine was dissolved and 1.0 g. of powdery potassium hydroxide was gradually added with stirring. After the addition, 2.7 g. of 2,4-dinitro-6-trifluoromethylchlorobenzene was added at 30° C. during 5 minutes to react them for about 3 hours. The reaction mixture was acidified with conc. HCl and the product was extracted with methylenechloride. The extracted layer was washed with water and dehydrated and the solvent was distilled. The product was separated by a silica gel column with an eluent of toluene and the solvent was distilled off to obtain 2.5 g. of the object compound having the melting point of 98° to 101° C.

PREPARATION 7

Preparation of N-(2-chloro-5-trifluoromethyl-6-pyridyl)-2,4-dinitro-6-trifluoromethylaniline In 20 ml. of dimethylformamide, 1.8 g. of 2-chloro-6-amino-5-trifluoromethylpyridine was dissolved and 1.0 g. of powdery potassium hydroxide was gradually added with stirring. After the addition, a solution of 2.7 g. of 2,4-dinitro-6-trifluoromethylchlorobenzene in 10 ml. of dimethylformamide was added dropwise at room temperature and the reaction was continued for about 3 hours. The reaction mixture was acidified with conc. HCl and was poured into water. The precipitate was filtered and recrystallized from methanol to obtain 2.9

PREPARATION 8

Preparation of N-(3,5-dichloro-4,6-dimethyl-2-pyridyl)-2,4-dinitro-6-trifluoromethylaniline In 20 ml. of dimethylformamide, 1.9 g. of 2-amino-3,5-dichloro-4,6-dimethylpyridine was dissolved and 0.7 g. of powdery potassium hydroxide was gradually added with stirring and a solution of 2.7 g. of 2,4-dinitro-6-trifluoromethylchlorobenzene in 10 ml. of dimethylformamide was added dropwise at room temperature to react them for about 10 hours. The reaction mixture was treated as the process of Preparation No. 7 to obtain 1.6 g. of the object compound having the melting point of 131° to 133° C.

PREPARATION 9

Preparation of N-(5-methoxy-2-pyridyl)-2,4-dinitro-6-trifluoromethylaniline

In accordance with the process of Preparation 8 except using 1.2 g. of 2-amino-5-methoxypyridine and 2.8 g. of 2,4-dinitro-6-trifluoromethylchlorobenzene, the reaction was carried out for 5 hours. The reaction mixture was treated as the process of Preparation 6 to obtain 1.2 g. of the object compound having the melting point of 102° to 105° C.

PREPARATION 10

Preparation of N-(3-chloro-5-trifluoromethyl-2-pyridyl)-2,4-dinitro-3-methoxy-6-trifluoromethylaniline In accordance with the process of Preparation 8 except using 1.9 g. of 2-amino-3-chloro-5-trifluoromethylpyridine and 2.8 g. of 2,4-dinitro-3-methoxy-6-trifluoromethylchlorobenzene, the reaction was carried out for 3 hours. The reaction mixture was treated as the process of Preparation 6 to obtain 1.4 g. of the object oily compound.

PREPARATION 11

Preparation of N-(3-chloro-5-trifluoromethyl-2-pyridyl)-2,6-dinitro-3-ethoxy-4-trifluoromethylaniline In 30 ml. of ethanol, 1.5 g. of sodium hydride was added with stirring and a solution of 7.0 g. of N-(3-chloro-5-trifluoromethyl-2-pyridyl)-2,6-dinitro-3-chloro-4-trifluoromethylaniline (obtained in Preparation 4) in 50 ml. of dimethylsulfoxide was added dropwise to react them at room temperature for 3 hours. The reaction mixture was poured into water and the product was extracted with methylene chloride. The extracted layer was washed with water and dehydrated and the solvent was distilled, the product was separated by a silica gel column with an eluent of a mixture of n-hexane and ethyl acetate (4:1) and the solvent was distilled off to obtain 4.0 g. of the object compound having the melting point of 106° to 108° C.

PREPARATION 12

Preparation of N-acetyl-N-(3-chloro-5-trifluoromethyl-2-pyridyl)-2,6-dinitro-3-chloro-4-trifluoromethylaniline In 20 ml. of pyridine, 2.3 g. of N-(3-chloro-5-trifluoromethyl-2-pyridyl)-2,6-dinitro-3-chloro-4-trifluoromethylaniline (obtained in Preparation 4) was dissolved and a solution of 0.34 g. of acetylchloride in 10 ml. of pyridine was added dropwise to react them at 60° to 70° C. for 2 hours. Pyridine was distilled off from the reaction mixture and the product was separated by a silica gel column with an eluent of n-hexane and ethyl acetate (4:1) and the solvent was distilled off to obtain 0.8 g. of the object compound having the melting point of 75° to 77° C.

The typical pyridylanilines having the formula (III) are shown.

$$X_n\text{-pyridyl-NH-aryl}(NO_2)_2(Y_1)(CF_3) \quad (III)$$

| Compound No. | $X_n$ | Position of pyridine ring | $Y_1$ | Property melting point(°C.) |
|---|---|---|---|---|
| 1 | 5-Cl | 2 | H | 104–106 |
| 2 | 3-Cl—5-CF$_3$ | 2 | H | 104–105 |
| 3 | 3,5-Cl$_2$ | 2 | H | 85–87 |
| 4 | 3,5-Cl$_2$ | 2 | Cl | 64–65 |
| 5 | 5-Cl | 2 | Cl | 143–144 |
| 6 | 4,6-Cl$_2$ | 2 | Cl | 194–196 |
| 7 | 3-Cl—5-CF$_3$ | 2 | Cl | 100–102 |
| 8 | 3,5-Cl$_2$—6-CH$_3$ | 2 | Cl | 128–130 |
| 9 | 3,5-Cl$_2$—4,6-(CH$_3$)$_2$ | 2 | H | 184–185 |
| 10 | 4-CH$_3$—5-Br | 2 | Cl | 98–100 |
| 11 | 3,5-Cl$_2$—4,6-(CH$_3$)$_2$ | 2 | Cl | 146–148 |
| 12 | 3,5-Cl$_2$—4-CH$_3$ | 2 | Cl | 135–137 |
| 13 | 3,5-Cl$_2$—4-CH$_3$ | 2 | H | 116–118 |
| 14 | 2,6-Cl$_2$ | 3 | Cl | 166–168 |
| 15 | 3,5-Cl$_2$ | 4 | H | 138–140 |
| 16 | 3,5-Cl$_2$ | 4 | Cl | 129–130 |
| 17 | 3,5-Br$_2$ | 2 | Cl | 144–147 |
| 18 | 3-Br—5-Cl | 2 | Cl | 131–133 |
| 19 | 5-CF$_3$ | 2 | Cl | oily ($n_D^{25}$ 1.571) |
| 20 | 3-Cl—5-Br | 2 | Cl | 119–121 |
| 21 | 3-Br—5-CF$_3$ | 2 | Cl | 89–92 |
| 22 | 3-Br—5-CF$_3$ | 2 | H | 112–114 |
| 23 | 5-Br—6-C$_2$H$_5$ | 2 | Cl | 137–139 |
| 24 | 5-Br—6-C$_2$H$_5$ | 2 | H | 146–148 |
| 25 | 2,6-(OCH$_3$)$_2$ | 3 | H | 153–155 |
| 26 | 3-CF$_3$—5-Br—6-Cl | 2 | H | 130–132 |
| 27 | 3-CF$_3$—5-Cl | 2 | H | 113–115 |
| 28 | 3-CF$_3$—5-Br | 2 | H | 104–106 |
| 29 | 3-CF$_3$—5-Cl | 2 | Cl | 138–140 |
| 30 | 3-CF$_3$—5-Br | 2 | Cl | 110–112 |
| 31 | 3-CF$_3$—5-Br—6-Cl | 2 | Cl | 48–52 |
| 32 | 3-Br—5-CF$_3$—6-Cl | 2 | H | 190–192 |
| 33 | 3-Br—5-CF$_3$—6-Cl | 2 | Cl | 156–160 |
| 34 | 3-Cl—5-CF$_3$—6-Cl | 2 | H | 150–154 |
| 35 | 3-Cl—5-CF$_3$—6-Cl | 2 | Cl | 144–145 |
| 36 | 3-CF$_3$ | 2 | Cl | oily |
| 37 | 3-CF$_3$ | 2 | H | 81–83 |
| 38 | 3-Cl—5-CF$_3$ | 2 | F | 127–129 |

The typical pyridylanilines having the formula (X) are shown.

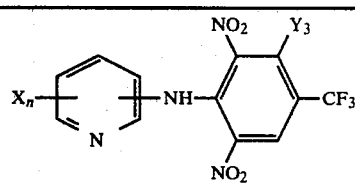

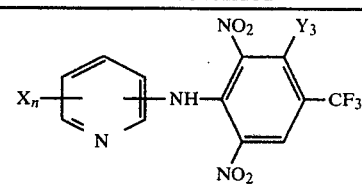

(X)

| Compound No. | $X_n$ | Position of pyridine ring | $Y_3$ | Property melting point(°C.) |
|---|---|---|---|---|
| 39 | 3-Cl—5-CF$_3$ | 2 | OCH$_3$ | 71–73 |
| 40 | " | 2 | OC$_2$H$_5$ | 106–108 |
| 41 | " | 2 | OC$_3$H$_7$(n) | 102–104 |
| 42 | " | 2 | OC$_3$H$_7$(iso) | 138–139 |
| 43 | " | 2 | OC$_4$H$_9$(n) | 109–110 |
| 44 | " | 2 | OC$_4$H$_9$(iso) | 123–124 |
| 45 | " | 2 | SCH$_3$ | 138–139 |
| 46 | " | 2 | SC$_2$H$_5$ | oily |
| 47 | " | 2 | OH | 183–187 |
| 48 | " | 2 | 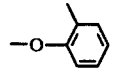 | 178–182 |
| 49 | " | 2 | —O—⟨⟩—OH | 162–165 |
| 50 | " | 2 | —O—⟨⟩(OH) | 78–81 |
| 51 | " | 2 | —N$_3$ | oily |

The typical pyridylanilines having the formula (I) except the compounds (III) and (X) are shown.

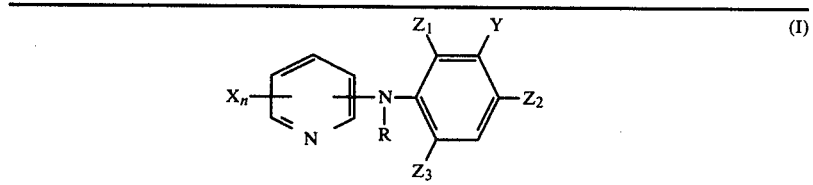

(I)

| Comp. No. | $X_n$ | Position of pyridine ring | R | Y | $Z_1$ | $Z_2$ | $Z_3$ | Property melting point(°C.) |
|---|---|---|---|---|---|---|---|---|
| 52 | 5-Cl | 2 | H | H | NO$_2$ | NO$_2$ | CF$_3$ | 133–135 |
| 53 | 5-I | 2 | " | " | " | " | " | 170–172 |
| 54 | 5-Br | 2 | " | " | " | " | " | 137–140 |
| 55 | 2-Cl | 3 | " | " | " | " | " | 125–126 |
| 56 | 4-CH$_3$ | 2 | " | " | " | " | " | 134–135 |
| 57 | 5-CF$_3$ | 2 | " | " | " | " | " | oily |
| 58 | — | 3 | " | " | " | " | " | $n_D^{30}$ 1.556 |
| 59 | — | 4 | " | " | " | " | " | 44–45 |
| 60 | 3,5-Cl$_2$ | 2 | " | " | " | " | " | 98–101 |
| 61 | 3,5-Br$_2$ | 2 | " | " | " | " | " | 161–164 |
| 62 | 3-Br—5-Cl | 2 | " | " | " | " | " | 106–108 |
| 63 | 3-Cl—5-Br | 2 | " | " | " | " | " | 89–91 |
| 64 | 3-Br—5-CH$_3$ | 2 | " | " | " | " | " | 123–125 |
| 65 | 3-Cl—5-CF$_3$ | 2 | " | " | " | " | " | 74–77 |
| 66 | 2-Cl—5-CF$_3$ | 6 | " | " | " | " | " | 129–131 |
| 67 | 5-I—6-C$_2$H$_5$ | 2 | " | " | " | " | " | 127–130 |
| 68 | 3,5-Cl$_2$—6-CH$_3$ | 2 | " | " | " | " | " | 72–75 |
| 69 | 5-Cl—6-CH$_3$ | 2 | " | " | " | " | " | 167–168 |
| 70 | 5-CF$_3$—6-Cl | 2 | " | " | " | " | " | 195–196 |
| 71 | 4,6-(CH$_3$)$_2$ | 2 | " | " | " | " | " | 146–147 |
| 72 | 4,6-Cl$_2$ | 2 | " | " | " | " | " | 169–170 |
| 73 | 4-Cl—6-CH$_3$ | 2 | " | " | " | " | " | 163–165 |
| 74 | 5-OCH$_3$ | 2 | " | " | " | " | " | 102–105 |
| 75 | 2,6-Cl$_2$ | 3 | " | " | " | " | " | 107–110 |
| 76 | 3-CF$_3$—6-Cl | 2 | " | " | " | " | " | oily |
| 77 | 3,5-Cl$_2$—4,6-(CH$_3$)$_2$ | 2 | " | " | " | " | " | 131–133 |
| 78 | 3,5-Cl$_2$—4-CH$_3$ | 2 | " | " | " | " | " | 166–169 |
| 79 | 3,5-Cl$_2$ | 4 | " | " | " | " | " | 141–142 |
| 80 | 3-Br—5-CF$_3$ | 2 | " | " | " | " | " | oily |
| 81 | 3-CF$_3$ | 2 | " | " | " | " | " | 106–108 |
| 82 | 3-CF$_3$—5-Br—6-Cl | 2 | " | " | " | " | " | oily |
| 83 | 3-CF$_3$—5-Cl | 2 | " | " | " | " | " | 120–122 |
| 84 | 3-CF$_3$—5-Br | 2 | " | " | " | " | " | 146–148 |
| 85 | 3-Cl—5-CF$_3$ | 2 | " | OCH$_3$ | " | " | " | oily |
| 86 | 3,5-Cl$_2$ | 2 | " | " | " | " | " | oily |
| 87 | 4-CH$_3$—5-Br | 2 | " | H | " | " | " | 58–60 |
| 88 | 3-Cl—5-CF$_3$ | 2 | —COCH$_3$ | Cl | " | CF$_3$ | NO$_2$ | 75–77 |
| 89 | 3-Cl—5-CF$_3$ | 2 | H | H | CF$_3$ | " | " | oily |
| 90 | 3,5-Cl$_2$ | 2 | " | " | " | " | " | 92–94 |
| 91 | 3-CF$_3$—5-Br—6-Cl | 2 | " | " | " | " | " | oily |

-continued

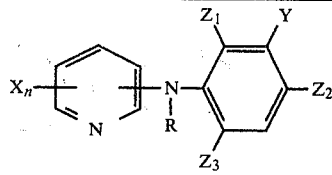
(I)

| Comp. No. | $X_n$ | Position of pyridine ring | R | Y | $Z_1$ | $Z_2$ | $Z_3$ | Property melting point(°C.) |
|---|---|---|---|---|---|---|---|---|
| 92 | 5-CF$_3$—6-Cl | 2 | " | " | " | " | " | 142–144 |
| 93 | 5-Cl | 2 | " | " | " | " | " | oily |
| 94 | 3-CF$_3$—6-Cl | 2 | " | " | " | " | " | 157–159 |
| 95 | 3-Cl—5-Cl—6-CH$_3$ | 2 | " | " | " | " | " | 110–111 |
| 96 | 4-CH$_3$—5-Br | 2 | " | " | " | " | " | oily |
| 97 | 3-Br—5-Cl | 2 | " | " | " | " | " | 96–98 |
| 98 | 3-Cl—5-Br | 2 | " | " | " | " | " | 87–90 |
| 99 | 3-CF$_3$—6-Cl | 2 | " | " | " | " | " | 83–86 |
| 100 | 5-CF$_3$—6-Cl | 2 | " | " | " | " | " | 162–165 |
| 101 | 3,5-Cl$_2$ | 2 | " | " | " | " | " | 73–75 |
| 102 | 3-Cl—5-CF$_3$ | 2 | " | " | " | " | " | oily |

TEST 1

In each unglazed pot having a diameter of 9 cm, rice plant (Chukyo Asahi) was cultured. At 3 leaf stage of the rice seedlings, 10 ml. of each solution of each active ingredient having a concentration of 100 ppm was sprayed by a spray gun. After maintaining the pot in a green-house at 24° to 25° C. for one day, each spore suspension of Pyricularia orzae was sprayed. Five days after the inoculation, number of lesions on the third leaf of seedling was observed. The protective value was calculated by the following equation:

$$\text{Protective value (\%)} = \left(1 - \frac{\text{number of lesions in treated pot}}{\text{number of lesions in non-treated pot}}\right) \times 100$$

The results are shown in Table 1.

TABLE 1

| Comp. No. | Protective value (%) | Comp. No. | Protective value (%) | Comp. No. | Protective value (%) |
|---|---|---|---|---|---|
| 1 | 91 | 18 | 100 | 35 | 95 |
| 2 | 100 | 19 | 100 | 36 | 100 |
| 3 | 100 | 20 | 100 | 37 | 100 |
| 4 | 100 | 21 | 100 | 38 | 100 |
| 5 | 100 | 22 | 100 | 39 | 100 |
| 7 | 100 | 23 | 93 | 40 | 100 |
| 8 | 100 | 24 | 90 | 41 | 95 |
| 9 | 83 | 25 | 85 | 42 | 95 |
| 10 | 86 | 26 | 100 | 43 | 95 |
| 11 | 84 | 27 | 100 | 44 | 95 |
| 12 | 100 | 28 | 100 | 45 | 100 |
| 13 | 92 | 29 | 100 | 46 | 95 |
| 14 | 100 | 30 | 100 | 47 | 95 |
| 15 | 100 | 32 | 100 | | |
| 16 | 100 | 33 | 100 | | |
| 17 | 100 | 34 | 100 | | |

In accordance with the test, except using each solution of each active ingredient having a concentration of 50 ppm, each test was carried out. Compound Nos. 54, 60, 61, 64, 65, 67, 68, 69, 75, 76, 78, 80, 81, 82, 83, 84, 85, 86, 87, 92 and 100 were used. The protective values were respectively 100.

In the test, the concentration of the active ingredient was varied and Compound No. 7 was compared with N-(2,6-difluoro-3,5-dichloro-4-pyridyl)-N-(4-nitro-2-trifluoromethylphenyl)amine (hereinafter referring to as Reference Compound) disclosed in U.S. Pat. No. 3,965,109, No. 4,140,778 and No. 3,926,611. The results are shown in Table 2.

TABLE 2

| Compound No. | Protective value (%) 25 ppm | Protective value (%) 12.5 ppm |
|---|---|---|
| Comp. No. 7 | 100 | 98 |
| Reference compound | 0 | 0 |

TEST 2

In each unglazed pot having a diameter of 9 cm, rice plant (Chukyo Asahi) was cultured. At 5 leaf stage of the rice seedlings, 20 ml. of each solution of each active ingredient having a concentration of 100 ppm was sprayed by a spray gun. After maintaining the pot in a green-house at 24° to 25° C. for one day, rice straw on which Rhizoctonia solani was cultured was held on sheath for inoculation. The pot was kept in an inoculation chamber at 30° C. and a humidity of 100% for 5 days. Each length of lesions of five stems per pot was measured. The protective value was calculated by the following equation:

$$\text{Protective value (\%)} = \left(1 - \frac{\text{total length of lesions in treated pot}}{\text{total length of lesions in non-treated pot}}\right) \times 100$$

The results are shown in Table 3.

TABLE 3

| Comp. No. | Preventive value (%) | Comp. No. | Preventive value (%) | Comp. No. | Preventive value (%) |
|---|---|---|---|---|---|
| 2 | 100 | 35 | 100 | 62 | 100 |
| 3 | 100 | 36 | 92 | 63 | 100 |
| 4 | 93 | 37 | 100 | 64 | 100 |
| 6 | 100 | 39 | 100 | 65 | 100 |
| 7 | 100 | 40 | 100 | 68 | 100 |
| 8 | 90 | 41 | 95 | 72 | 100 |
| 14 | 100 | 42 | 95 | 73 | 87 |
| 15 | 100 | 43 | 95 | 74 | 93 |
| 16 | 100 | 44 | 95 | 75 | 100 |
| 18 | 100 | 45 | 100 | 76 | 100 |
| 19 | 100 | 47 | 95 | 78 | 100 |

TABLE 3-continued

| Comp. No. | Preventive value (%) | Comp. No. | Preventive value (%) | Comp. No. | Preventive value (%) |
|---|---|---|---|---|---|
| 26 | 100 | 48 | 100 | 79 | 90 |
| 29 | 100 | 49 | 100 | 80 | 100 |
| 30 | 95 | 50 | 100 | 85 | 100 |
| 31 | 90 | 51 | 95 | 86 | 100 |
| 32 | 100 | 54 | 90 | 87 | 100 |
| 33 | 100 | 60 | 100 | 88 | 100 |
| 34 | 100 | 61 | 100 | | |

TEST 3

In each unglazed pot having a diameter of 9 cm, cucumber plant (Suyo) was cultured. At one leaf stage, 10 ml. of each solution of each active ingredient having a concentration of 500 ppm was sprayed by a spray gun. After maintaining the pot in a green-house at 24° to 25° C. for one day, each spore suspension of *Collectotrichum lagenarium* was sprayed. Six days after the inoculation, number of lesions on the first leaf of seedling was observed. The protective value was calculated as Test 1. The results are shown in Table 4.

TABLE 4

| Compound No. | Protective value (%) |
|---|---|
| Comp. 3 | 100 |
| 4 | 100 |
| 7 | 100 |
| 8 | 100 |
| 12 | 75 |
| 14 | 100 |
| 26 | 90 |

TEST 4

In each unglazed pot having a diameter of 9 cm, cucumber plant (Suyo) was cultured. At one leaf stage, 10 ml. of each solution of each active ingredient having a concentration of 500 ppm was sprayed by a spray gun. After maintaining the pot in a green-house at 24° to 25° C. for one day, spores of *Sphaerotheca fuliginea* (obtained from the *Sphaerotheca fuliginea* seedlings) were inoculated. Ten days after the inoculation, number of lesions on the first leaf of seedling was measured.

The protective value was calculated as Test 1. The results are shown in Table 5.

TABLE 5

| Comp. No. | Protective value (%) | Comp. No. | Protective value (%) | Comp. No. | Protective value (%) |
|---|---|---|---|---|---|
| 3 | 100 | 16 | 100 | 31 | 100 |
| 7 | 100 | 21 | 100 | 32 | 100 |
| 14 | 95 | 22 | 100 | 33 | 100 |
| 15 | 100 | 26 | 100 | 34 | 100 |
| | | | | 51 | 100 |

When each solution having a concentration of 100 ppm was sprayed in the test, the protective values of Compound No. 62 and No. 66 were respectively 100.

TEST 5

A mixture of 9 ml. of a potato-glucose-agar medium (PDA medium) and 1 ml. of each active ingredient was poured into each Petri-dish to be solidified. An agar disc on which various fungi were cultured was put on the medium to keep it at the optimum temperature for the specific days, the growths of mycelia were observed to determine the minimum growth inhibition concentration of the active ingredient to these fungi. The following fungi were used.

A: *Phytophthora infestans*
B: *Diaporthe citri*
C: *Alternaria solani*
D: *Venturia inaequalie*.

The results are shown in Table 6.

TABLE 6

| Infestans | A | B | C | D |
|---|---|---|---|---|
| Comp. No. 3 | 100 | 100 | 10 | <1 |
| 4 | >100 | 100 | 100 | <1 |
| 7 | 100 | <1 | <1 | <1 |

TEST 6

Young seedling of kidney bean treated to cut off leaves except one primordial leaf was transplanted in a cup and about 30 of larvae and adults of *Tetranychus telarius* (L) were inoculated on the primordial leaf. This was dipped for 10 seconds in each solution obtained by diluting each wettable powder of Composition No. 5 containing each active ingredient with water at the concentration of 800 ppm and was dried in air and was kept in a constant temperature chamber with lighting at 28° C. Three days after the treatment, mortality was measured and each percent mortality was calculated as follows.

$$\text{Percent mortality (\%)} = \frac{\text{number of mortal mites}}{\text{Total number of mites}} \times 100$$

The results are shown in Table 7.

TABLE 7

| Comp. No. | Percent mortality (%) | Comp. No. | Percent mortality (%) | Comp. No. | Percent mortality (%) |
|---|---|---|---|---|---|
| 3 | 100 | 37 | 100 | 101 | 100 |
| 15 | 100 | 39 | 100 | 102 | 100 |
| 22 | 100 | 40 | 100 | Ref | |
| 26 | 100 | 41 | 100 | Comp. | 40 |
| 27 | 100 | 49 | 100 | | |
| 28 | 100 | 89 | 100 | | |
| 29 | 100 | 90 | 100 | | |
| 34 | 100 | 100 | 100 | | |

TEST 7

Each active ingredient was dissolved in acetone to prepare each solution having the specific concentration. 1 Ml. of the solution (400 μg. of each active ingredient) was uniformly adhered on the inner bottom surface of Petri-dish having a diameter of 9 cm to form a film. In the dish, 15 of adults of *Callosobruchus chinensis* were charged and the dish was covered with a cap and kept in a constant temperature chamber at 25° C. for 24 hours. Each percent mortality was calculated as that of Test 6. The results are shown in Table 8.

TABLE 8

| Comp. No. | Percent mortality (%) | Comp. No. | Percent mortality (%) |
|---|---|---|---|
| 2 | 100 | 62 | 100 |
| 3 | 100 | 63 | 100 |
| 52 | 100 | 65 | 100 |
| 54 | 100 | 70 | 100 |
| 60 | 100 | 77 | 100 |

TABLE 8-continued

| Comp. No. | Percent mortality (%) | Comp. No. | Percent mortality (%) |
| --- | --- | --- | --- |
| 61 | 100 | 81 | 100 |

TEST 8

Each minimum growth inhibition concentration (MIC) of Compound No. 16 to various microorganisms was measured by the agar dilution process. The results are shown in Table 9. In the cases of bacteria, the results were observed 24 hours after the inoculation and in the cases of fungi, the results were observed 1 week after the inoculation.

TABLE 9

| Microorganism | Medium | MIC (ppm) |
| --- | --- | --- |
| Bacillus subtilis PC1219 | Bouillon | <0.2 |
| Staphylococcus aureus 209P | agar | <0.2 |
| Escherichia coli | medium | 12.5 |
| Salmonella typhimurium IFO 12529 | | 6.25 |
| Klebsiella pneumoniae IFO 3512 | | 12.5 |
| Serratia marcescens IFO 12648 | | 6.25 |
| Proteus morganii IFO 3848 | | 6.25 |
| Pseudomonas aeruginosa | | 12.5 |
| Penicillium italicum | Sabouraud's | 3.12 |
| Penicillium chrysogeum IFO 4626 | agar medium | 3.12 |
| Penicillium citrium IFO 6352 | | 6.25 |
| Penicillium funiculosum IFO 6354 | | 6.25 |
| Aspergillum niger IFO 6341 | | 3.12 |
| Aspergillum fumigatus IFO 4057 | | 6.25 |
| Aspergillum flavus IFO 6343 | | 6.25 |
| Aureobasidium pullulans IFO 6353 | | 6.25 |
| Chaetomium globosum IFO 6347 | | 3.12 |
| Gliocladium virens IFO 9166 | | 12.5 |
| Myrothecium verrucaria IFO 6133 | | 6.25 |
| Gibberella fujikuroi IFO 6349 | | 12.5 |
| Trametes sanguinea | | 6.25 |

TEST 9

In each unglazed pot having a diameter of 9 cm, cucumber plant (Suyo) was cultured. At one leaf stage, 10 ml. of each solution of each active ingredient having a concentration of 250 ppm was sprayed by a spray gun. After maintaining the pot in a green-house at 24° to 25° C. for one day, a disc (punched agar disc) obtained by culturing *Botrytis cinerea* on a potato-glucose-agar medium (PDA medium) was put on the leaf of cucumber to inoculate them. Three days after the inoculation, lengths of lesions were measured and each protective value was calculated as Test 2. The results are shown in Table 10.

TABLE 10

| Comp. No. | Protective value (%) | Comp. No. | Protective value (%) |
| --- | --- | --- | --- |
| 7 | 100 | 48 | 100 |
| 14 | 95 | 49 | 100 |
| 16 | 100 | 50 | 100 |
| 17 | 92 | | |
| 18 | 100 | | |
| 19 | 100 | | |
| 21 | 100 | | |
| 22 | 100 | | |
| 23 | 81 | | |
| 26 | 85 | | |
| 29 | 100 | | |
| 30 | 100 | | |
| 33 | 100 | | |
| 34 | 100 | | |
| 35 | 100 | | |
| 36 | 96 | | |
| 37 | 93 | | |

In accordance with the test, except the concentration of the active ingredient was decreased, the comparative tests of Compound No. 7 and Reference compound were carried out. The results are shown in Table 11.

TABLE 11

| Compound | Protective value (%) (62.5 ppm) |
| --- | --- |
| Compound No. 7 | 100 |
| Reference compound | 0 |

TEST 10

In each unglazed pot having a diameter of 9 cm, cucumber plant (Suyo) was cultured. At two leaf stage, 20 ml. of each solution of each active ingredient having a concentration of 500 ppm was sprayed by a spray gun. After maintaining the pot in a green-house at 24° to 25° C. for one day, each spore suspension of *Plasmopara viticola* was sprayed. Six days after the inoculation, number of lesions on the first seedling was observed. The protective value was calculated as Test 1. The results are shown in Table 12.

TABLE 12

| Compound No. | Protective value (%) |
| --- | --- |
| 4 | 100 |
| 7 | 100 |
| 20 | 100 |
| 26 | 93 |
| 33 | 85 |
| 34 | 83 |
| 51 | 100 |
| 88 | 100 |

TEST 11

Each emulsifiable concentrate of each active ingredient as Composition No. 3 was dispersed in water at a concentration of 800 ppm. Each leaf of cabbage was dipped into each emulsion for about 10 seconds and taken up and dried in air.

A wet filter paper was put in each Petri dish (diameter of 9 cm), and each treated leaf was put on the filter paper. Larvae of *Plutella xylostella* at 2nd to 3rd instar were charged and the dish was covered with a cap and kept in a constant temperature chamber with lighting at 28° C. Eight days after the charge, mortality was measured and each percent mortality was calculated. The results are shown in Table 13.

TABLE 13

| Comp. No. | Percent mortality (%) | Comp. No. | Percent mortality (%) | Comp. No. | Percent mortality (%) |
| --- | --- | --- | --- | --- | --- |
| 7 | 100 | 57 | 100 | 68 | 100 |
| 15 | 100 | 58 | 100 | 70 | 100 |
| 29 | 100 | 59 | 100 | 74 | 100 |
| 40 | 100 | 60 | 100 | 77 | 100 |
| 41 | 100 | 61 | 100 | 81 | 100 |
| 42 | 100 | 62 | 100 | 83 | 100 |
| 43 | 100 | 63 | 100 | 87 | 100 |
| 52 | 100 | 64 | 100 | Ref. | 0 |

TABLE 13-continued

| Comp. No. | Percent mortality (%) | Comp. No. | Percent mortality (%) | Comp. No. | Percent mortality (%) |
|---|---|---|---|---|---|
| 53 | 100 | 65 | 100 | comp. | |
| 55 | 100 | 66 | 100 | | |
| 56 | 100 | 67 | 100 | | |

The pyridylanilines of the present invention impart excellent effect for combatting noxious livings such as insects, mites, fungi and bacteria, for example, excellent antifungal and antibacterial effect for controlling noxious fungi and bacteria multiplicating on industrial products, seeds and fruits in storage such as *Aspergillus sp. Gibberella sp.* and *Penicillium sp.*

The pyridylanilines are also effective for controlling noxious living grown on agricultural and horticultural crops and up-land, for example, insects such as Lepidoptera as Plutella Xylostella, *Mamestra brassicae* and *Spodoptera litura;* Hemiptera as *Nephotettix cincticeps* and *Delphacodes striatella;* Coleoptera as *Callosobruchus chimensis* and *Epilachna vigintioctopunctata;* and Diptera such as *Musca domestica* and *Culexopipiens pallens;* and mites such as *Tetranychus urticae, Tetranychus telarius* and *Panonychus citri;* and fungi and bacteria for plants such as *Pyricularia oryzae, Rhizoctonia solani, Collectotrichum lagenarium, Pseudopernospora cubensis, Sphaerotheca fuliginea, Phytophthora infestans, Diaporthe citri, Alternaria solani, Venturia inaequalis, Plasmopara viticola, Botrytis cinerea, Puccinia recondita* and *Sclerotinia sclerotiorum.*

The pyridylanilines impart excellent effect for controlling various noxious livings especially noxious fungi to agricultural and horticultural plants.

The compounds having the formula (V) or (VII) are especially effective for agricultural and horticultural fields since the compounds impart excellent effect for controlling *Botrytis cinerea, Plasmopara viticola, Colletotrichum lagenarium, Sphaerotheca fuliginea, Pyricularia oryzae* and *Rhizoctonia solani* etc.

A concentration of pyridylaniline for the application was depending upon object noxious livings, a method of application, a form of the composition and a dose of the active ingredient and is not critical and it is usually in a range of 1 to 10,000 ppm preferably 20 to 2,000 ppm.

When the compounds are used as active ingredients of the insecticidal, acaricidal, fungicidal or bactericidal composition, it is possible to prepare various forms of the compositions such as dust, wettable powder, emulsifiable concentrate, inert emulsion, oil solution, aerosol preparation, etc. with adjuvants as the cases of agricultural compositions. The composition can be applied with or without diluting them in suitable concentrations.

Suitable adjuvants include powdery carries such as talc, kaolin, bentonite, diatomaceous earth, silicon dioxide, clay and starch; liquid diluents such as water, xylene, toluene, dimethylsulfoxide, dimethylformamide, acetonitrile, and alcohol; emulsifiers dispersing agents, spreaders etc.

The concentration of the active ingredient in the insecticidal acaricidal, fungicidal or bactericidal composition is usually 5 to 80 wt. % in the case of the oily concentrate; and 0.5 to 30 wt. % in the case of dust; 5 to 60 wt. % in the case of wettable powder. It is also possible to combine with the other agricultural ingredients such as the other insecticides, acaricides, plant growth regulators. Sometimes synergistic effects are found. The other agricultural ingredients include organic phosphoric acid ester type compounds, carbamate type compounds, dithio (or thiol) carbamate type compounds, organic chlorine type compounds, dinitro type compounds, organic sulfur or organometallic type compounds, antibiotics, substituted diphenyl ether type compounds, urea type compounds, triazine type compounds, benzoylurea type compounds, pyrethroid type compounds, imide type compounds and benzimidazole type compounds and more particularly, benzoylurea type insecticides such as N-(2,6-difluorobenzoyl)-N'-(p-chlorophenyl)urea; pyrethroid type insecticides such as α-cyano-3-phenoxybenzyl-2-(4-chlorophenyl) isovalerate; imide type germicides such as N-(3,5-dichlorophenyl)-1,2-dimethylcyclopropane-1,2-dicarboximide; benzimidazole type germicides such as methyl-1-(butylcarbamoyl)-2-benzimidazolecarbamate; thiocarbamate type germicides such as S-ethyl N-(3-dimethylaminopropyl)thiocarbamate hydrochloride; dithiocarbamate type germicides such as manganese ethylenebisdithiocarbamate; and urea type germicides such as 2-cyano-N-(ethylaminocarbonyl)-2-(methoxyimino)acetamide.

The agricultural fungicidal compositions are the typical compositions of the present invention.

The typical forms of the composition are the wettable powder and the emulsifiable concentrate. The typical compositions are as follows:

| Agricultural fungicidal composition (concentrate): | | |
|---|---|---|
| | Usual | Preferable |
| Active ingredient: | 2–80 wt. % | 5–80 wt. % |
| Liquid or solid carrier: | { Adjuvant | 10–95 wt. % |
| Surfactant: | 98–20 wt. % } | 1–20 wt. % |
| Wettable powder: | | |
| Active ingredient: | | 5–70 wt. % |
| Solid carrier: | | 10–90 wt. % |
| Surfactant: | | 3–20 wt. % |
| Emulsifiable concentrate: | | |
| Active ingredient: | | 5–80 wt. % |
| Liquid carrier: | | 10–95 wt. % |
| Surfactant: | | 3–20 wt. % |

Suitable adjuvants include powdery carries such as talc, kaolin, bentonite, diatomaceous earth, silicon dioxide, clay and starch; liquid carriers such as water, xylene, toluene, dimethylsulfoxide, dimethylformamide, acetonitrile, and alcohol; and surfactants such as sodium alkyl benzene sulfonate, polyoxyethylene alkylaryl ether, sodium naphthalene sulfonate formaldehyde condensate, calcium ether sulfate, polyoxyethyleneglycol dodecylphenyl ether, polyoxyethylene lauryl ether, polyoxyethylene fatty acid ester, sodium alkylsulfate, sulfate of polyoxyethylene alkylaryl ether and di-alkylsulfosuccinate etc.

| Composition No. 1: | |
|---|---|
| Active ingredient: | 20 wt. parts |
| Xylene: | 72 wt. parts |
| Polyoxyethylene alkylphenyl ether: | 8 wt. parts |

The components were uniformly mixed and dissolved to prepare an emulsifiable concentrate.

| Composition No. 2: | |
|---|---|
| Active ingredient: | 5 wt. parts |

-continued

| Composition No. 2: | |
|---|---|
| Talc: | 95 wt. parts |

The components were uniformly mixed to prepare a dust.

| Composition No. 3: | |
|---|---|
| Active ingredient: | 20 wt. parts |
| Xylene: | 60 wt. parts |
| Polyoxyethylenealkylaryl ether: | 20 wt. parts |

The components were mixed and dissolved to prepare an emulsifiable concentrate.

| Composition No. 4: | |
|---|---|
| Jeeklite: | 78 wt. parts |
| Sodium naphthalenesulfonate-aldehyde condensate: | 2 wt. parts |
| Mixture of polyoxyethylenealkyl-aryether sulfate and fine silicon dioxide (50:50): | 5 wt. parts |
| Fine silicon dioxide | 15 wt. parts |

A mixture of these components was mixed with each active ingredient at a ratio of 4:1 by weight to prepare a wettable composition.

| Compositon No. 5: | |
|---|---|
| Active ingredient: | 70 wt. parts |
| Jeeklite: | 10 wt. parts |
| Mixture of polyoxyethylene alkylaryl ether sulfate and fine silica (50:50): | 20 wt. parts |

The components were uniformly mixed and pulverized to prepare a wettable powder.

| Composition No. 6 | |
|---|---|
| Active ingredient: | 30 wt. parts |
| Sodium laurylsulfate: | 2 wt. parts |
| Sodium dinaphthylmethanesulfonate: | 3 wt. parts |
| Fine silicon dioxide (SiO$_2$ . nH$_2$O): | 20 wt. parts |
| Diatomaceous earth: | 45 wt. parts |

The components were uniformly mixed to prepare a wettable powder.

| Composition No. 7: | |
|---|---|
| Active ingredient: | 5 wt. parts |
| Xylene: | 91 wt. parts |
| Polyoxyethylenealkylphenyl ether: | 4 wt. parts |

The components were uniformly mixed to prepare an emulsifiable concentrate.

| Composition No. 8: | |
|---|---|
| Active ingredient: | 5 wt. parts |
| Fine silicon dioxide: | 10 wt. parts |
| Jeeklite: | 80 wt. parts |
| Mixture of polyoxyethylenealkylaryl ethersulfate and fine silicon dioxide (50:50): | 5 wt. parts |

The components were uniformly mixed and pulverized to prepare a wettable powder.

We claim:

1. A pyridylaniline compound represented by the following formula (I):

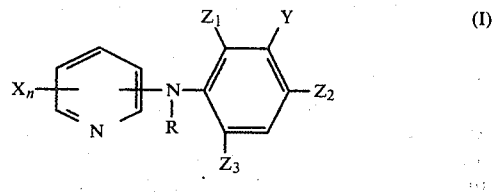

wherein X is a trifluoromethyl group, a halogen atom, a lower alkyl group or a lower alkoxy group; n is an integer of 1 to 4; R is a hydrogen atom or an acetyl group; Y is a hydrogen atom, a halogen atom, a lower alkoxy group, a lower alkylthio group or a hydroxy group; $Z_1$, $Z_2$ and $Z_3$ are a trifluoromethyl group or a nitro group, with the proviso that at least one X is trifluoromethyl and with the proviso that when the X substitution pattern is 3-chloro-5-trifluoromethyl, Y in addition optionally is azido or 2,3, or 4-hydroxyphenoxy.

2. The compound of claim 1, which is represented by the following formula (II)

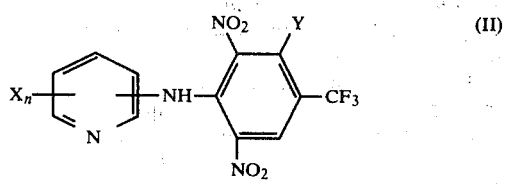

wherein X, Y and n are the same defined in the above formula (I).

3. The compound of claim 1, which is represented by the following formula (III)

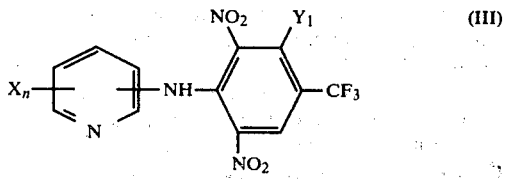

wherein X and n are the same defined in the above formula (I), $Y_1$ is a hydrogen atom or a halogen atom.

4. The compound of claim 1, which is represented by the following formula (IV)

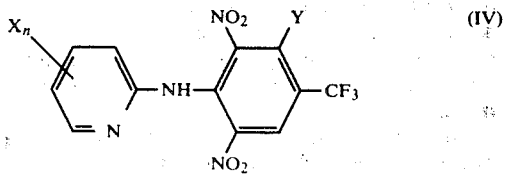

wherein X, Y and n are the same defined in the above formula (I).

5. The compound of claim 1 wherein the compound is an N-(3-chloro-5-trifluoromethyl-2-pyridyl)-2,6-dinitro-3-chloro-4-trifluoromethylaniline.

6. The compound of claim 1 wherein the compound is an N-(3-chloro-5-trifluoromethyl-2-pyridyl)-2,6-dinitro-3-(o-hydroxyphenoxy-4-trifluoromethylaniline.

7. The compound of claim 1 wherein the compound is an N-(3-chloro-5-trifluoromethyl-2-pyridyl)-2,6-dinitro-3-ethoxy-4-trifluoromethylaniline.

8. The compound of claim 1, which has the formula:

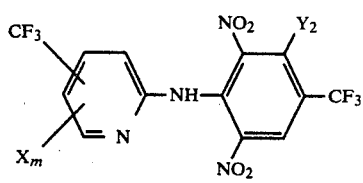

(V)

wherein $Y_2$ is hydrogen, lower alkoxy, or halogen, m is an integer of 0 to 3 and X is as defined in claim 1, with the proviso that when the pyridyl ring substitution pattern is 3-chloro-5-trifluoromethyl, $Y_2$ in addition, optionally is azido or 2,3 or 4-hydroxyphenoxy.

9. The compound of claim 8, which has the formula (VI):

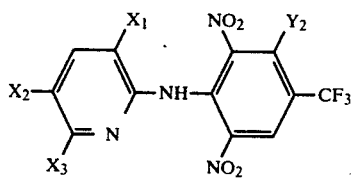

(VI)

wherein $X_1$ and $X_2$ are halogen or trifluoromethyl independently of each other; $X_3$ is hydrogen or halogen; and $Y_2$ is as defined in claim 8, with the proviso that when $X_1$ is chlorine, $X_2$ is trifluoromethyl and $X_3$ is hydrogen, $Y_2$ in addition, optionally is azido or 2,3 or 4-hydroxyphenoxy.

10. The compound of claim 8, which has the formula:

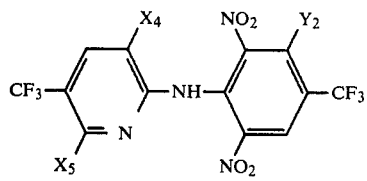

(VII)

wherein $X_4$ is halogen, $X_5$ is hydrogen or halogen, $Y_2$ is as defined in claim 8, with the proviso that when $X_5$ is hydrogen and $X_4$ is chlorine, $Y_2$ in addition, optionally is azido or 2,3 or 4-hydroxyphenoxy.

11. A composition for combatting insects, which comprises:
an effective insect growth inhibiting amount of the compound of claim 1 in admixture with an acceptable adjuvant.

12. A composition for combatting mites, which comprises:
an effective mite growth inhibiting amount of the compound of claim 1 in admixture with an acceptable adjuvant.

13. A composition for combatting fungus, which comprises:
an effective fungus growth inhibiting amount of the compound of claim 1 in admixture with an acceptable adjuvant.

14. A composition for combatting bacteria, which comprises:
an effective bacteria growth inhibiting amount of the compound of claim 1 in admixture with an acceptable adjuvant.

15. The composition according to claim 11, 12, 13 or 14 which comprises 2 to 80 wt.% of the pyridylaniline having the formula (I) and 98 to 20 wt.% of the agricultural adjuvant.

16. The agricultural fungicidal composition according to claim 29 which comprises 2 to 80 wt.% of the pyridylaniline having the formula (VII) and 98 to 20 wt.% of the agricultural adjuvant.

17. The composition according to claim 11, 12, 13 or 14 wherein the active ingredient is an N-(3-chloro-5-trifluoromethyl-2-pyridyl)-2,6-dinitro-3-chloro-4-trifluoromethylaniline.

18. The composition according to claim 11, 12, 13 or 14 wherein the active ingredient is an N-(3-chloro-5-trifluoromethyl-2-pyridyl)-2,6-dinitro-3-(o-hydroxyphenoxy)-4-trifluoromethylaniline.

19. The composition according to claim 11, 12, 13 or 14 wherein the active ingredient is an N-(3-chloro-5-trifluoromethyl-2-pyridyl)-2,6-dinitro-3-ethoxy-4-trifluoromethylaniline.

* * * * *